United States Patent [19]
Anderson et al.

[11] Patent Number: 5,514,113
[45] Date of Patent: May 7, 1996

[54] ANGLED SYRINGE NEEDLE AND ADAPTER THEREFOR

[76] Inventors: David Anderson, 609 E. Sunset Dr. N., Redlands, Calif. 92373; Auville Krause, 12286 Michigan St., Grand Terrace, Calif. 92324

[21] Appl. No.: 212,052

[22] Filed: Mar. 14, 1994

[51] Int. Cl.⁶ ..................................... A61M 5/32
[52] U.S. Cl. ................ 604/272; 604/239; 433/90
[58] Field of Search .................... 604/272–274, 604/239, 264, 51, 283, 254, 905, 240–243, 117, 162, 171; 433/89, 90; 606/166; 128/DIG. 26

[56] References Cited

U.S. PATENT DOCUMENTS

| | | | |
|---|---|---|---|
| 762,603 | 6/1904 | Witkowski | 604/273 X |
| 844,544 | 2/1907 | Schimmel | 604/241 |
| 881,469 | 3/1908 | Hale | 604/239 X |
| 964,950 | 7/1910 | Allinger | 604/241 |
| 1,125,887 | 1/1915 | Schimmel | 604/239 X |
| 1,503,399 | 7/1924 | Webb | 604/273 |
| 1,569,961 | 1/1926 | Bauchert | 604/241 |
| 2,531,730 | 11/1950 | Henderson | 604/264 |
| 3,026,616 | 3/1962 | Clark | 433/90 |
| 3,175,557 | 3/1965 | Hammond | 604/264 X |
| 3,326,206 | 6/1967 | Barr, Sr. et al. | 604/413 X |
| 3,436,828 | 4/1969 | Dragan | 433/90 |
| 3,738,006 | 6/1973 | Lopez et al. | 433/90 |
| 3,788,320 | 1/1974 | Dye | 604/272 X |
| 3,874,383 | 4/1975 | Glowacki | 604/240 X |
| 3,994,295 | 11/1976 | Wulff | 604/241 |
| 4,515,583 | 5/1985 | Sovich | 604/22 |
| 4,518,383 | 5/1985 | Evans | 604/51 |
| 4,723,947 | 2/1988 | Konopka | 604/272 |
| 4,834,722 | 5/1989 | Zenz | 604/272 |
| 4,958,901 | 9/1990 | Coombs | 604/44 |
| 5,199,445 | 4/1993 | Rubinfeld | 128/898 |
| 5,284,476 | 2/1994 | Koch | 604/274 |
| 5,336,088 | 8/1994 | Discko, Jr. | 433/90 |

*Primary Examiner*—C. Fred Rosenbaum
*Assistant Examiner*—V. Alexander
*Attorney, Agent, or Firm*—Richard C. Litman

[57] ABSTRACT

A syringe and adapter are constructed so as to provide a bend in the hypodermic needle allowing a dentist to reach hard to get to places inside the mouth. With a bend in the needle, the dentist can rotate the body of the syringe to point the needle in various directions while the body of the syringe is placed inside the mouth. Around the bend of the needle is a solid material to prevent the needle from breaking about the bend while in use.

7 Claims, 2 Drawing Sheets

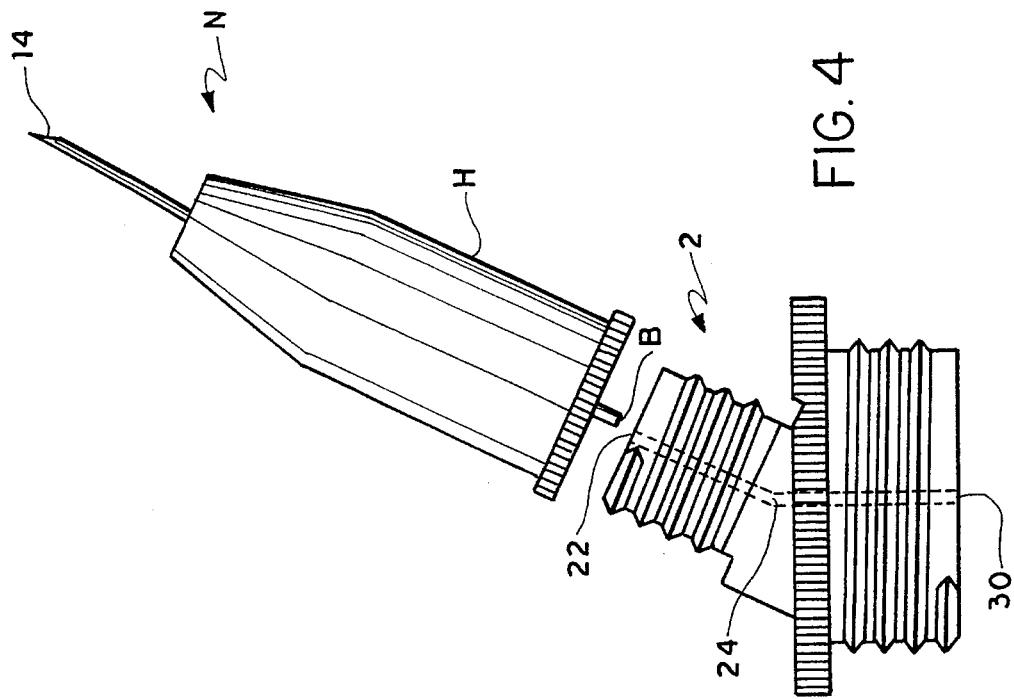
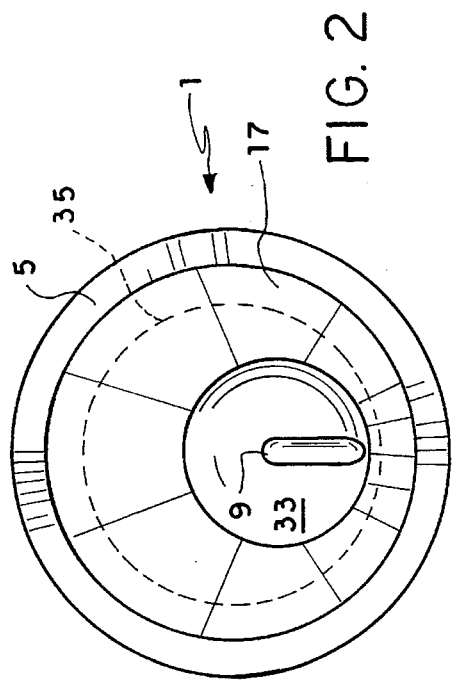
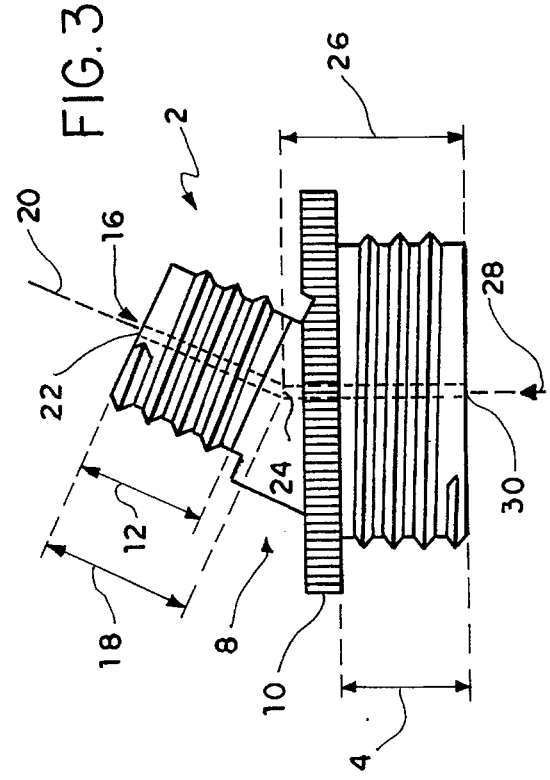

ANGLED SYRINGE NEEDLE AND ADAPTER THEREFOR

BACKGROUND OF THE INVENTION

1. Field of the Invention

The present invention pertains to an angled syringe needle and adapter therefor. More particularly, the present invention pertains to an angled syringe needle and adapter therefor in which the bend in the needle is surrounded by a solid material to prevent flexing of the needle around the bend portion while in use.

2. Description of the Prior Art

U.S. Pat. No. 1,384,355 issued Jul. 12, 1921 to Arthur E. Smith discloses a hypodermic needle having a hub attachable to a syringe and a nozzle extending from said hub with a top portion thereof including a bend portion to which a needle is attached.

U.S. Pat. No. 3,046,985 issued Jul. 31, 1962 to Candelario Saenz discloses a dental syringe adapter attachable to the back end of an existing dental syringe.

U.S. Pat. No. 3,520,292 issued Jul. 14, 1970 to Courtland H. Barr, Sr. et al discloses a blood pilot tube holder having a needle having two bend portions within a solid portion thereof.

U.S. Pat. No. 4,723,947 issued Feb. 9, 1988 to April A. Konopka discloses a intravenous injection needle having a bend portion.

None of the above inventions and patents, taken either singly or in combination, is seen to describe the instant invention as claimed.

SUMMARY OF THE INVENTION

The angled syringe needle and adapter therefor facilitates the ease of injecting most dental anesthesia by the dentist. The needle comes off the end of the syringe at an angle with respect to the longitudinal axis of the plunger allowing the dentist to apply a force on the plunger along one axial direction thereof while injecting the anesthesia through the aperture of the needle along a different axial direction of the aperture. This allows the dentist to operate the plunger at a convenient angle while allowing the needle access to the inside walls of the mouth.

Accordingly, it is a principal object of the invention to provide an angled syringe and adapter therefore allowing the dentist to easily inject anesthesia at any location within the mouth of a patient.

It is another object of the present invention to provide such syringes and adapters which are small and light weight.

It is a further object of the present invention to provide solid structure around the bend of the needle to prevent the needle from breaking at the bend due to a flexing of the needle about the bend during use.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

FIG. 2 is a top view of the angled syringe needle of the present invention.

FIG. 3 is a side view of the angled syringe needle adapter of the present invention.

FIG. 4 is a side exploded view of the angled syringe needle adapter of the present invention with a syringe needle of the prior art located thereabove.

Similar reference characters denote corresponding features consistently throughout the attached drawings.

DETAILED DESCRIPTION OF THE PREFERRED EMBODIMENTS

Figure 1:
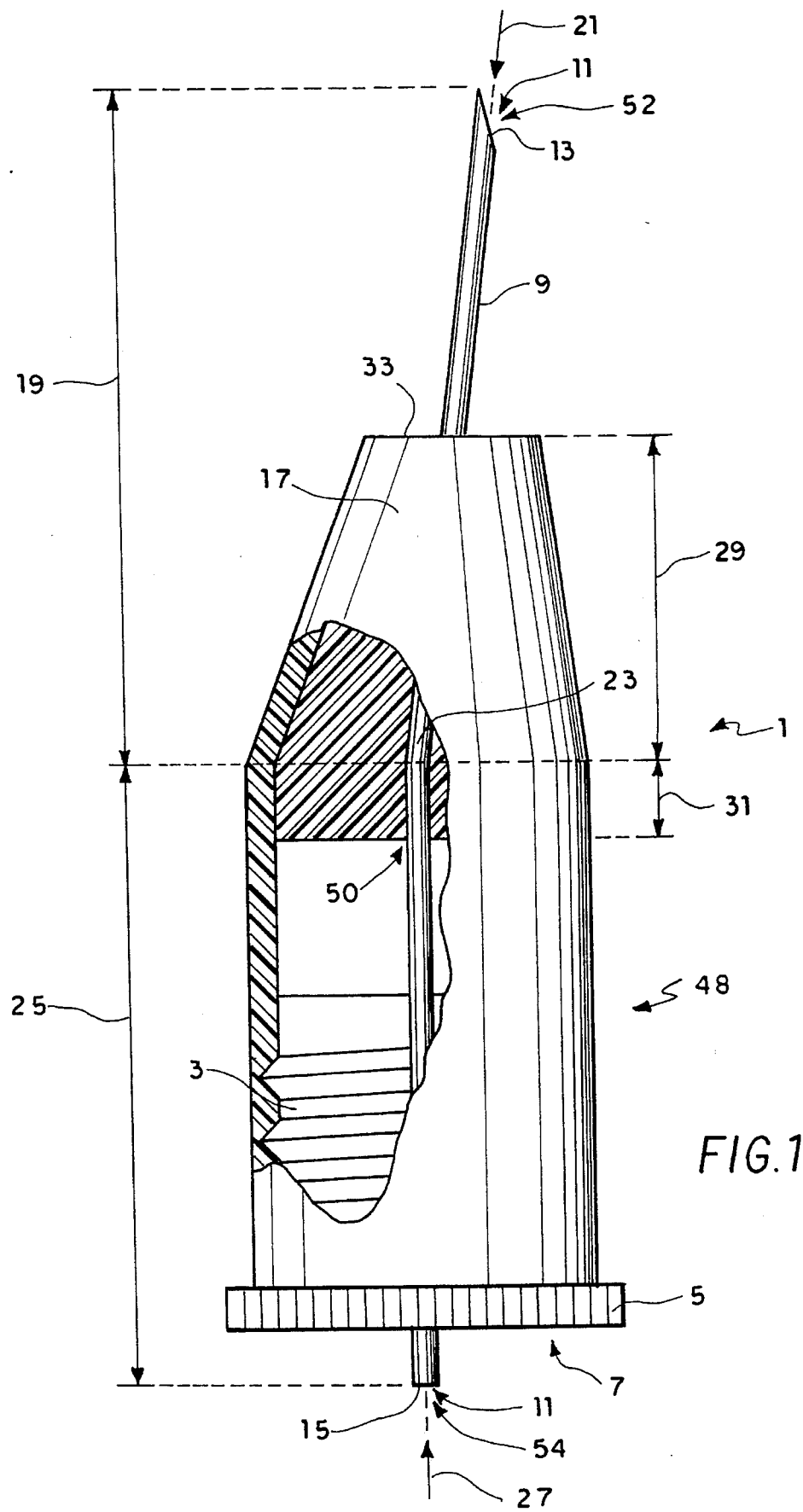
FIG. 1 is side view of the angled syringe needle assembly of the present invention.

As shown in FIG. 1, the angled syringe needle 1 of the present invention includes a main body portion 48 having an internally threaded cylindrical hub 3 and a solid tip portion 17. The hub 3 is hollow and includes a flanged beaded grip 5 over the bottom open end 7 of the hub 3. The hub 3 is made of a solid rigid material such as aluminum or plastic. The solid tip portion 17 includes a channel 50 therethrough. A needle 9 having an aperture 11 therethrough extends from a bevelled top end 13 through the solid tip portion 17 of the needle 1 then through the hub 3 to a bottom end 15 of the needle 9. A first portion 19 of the needle 9 extends from its top end 13 along a first longitudinal axis 21 to a bend portion 23. A second portion 25 of the needle 9 extends from the bend portion 23 along a second longitudinal axis 27, through the bottom end of the tip 17, into the hub 3 and out the back open end 7 of the hub 3 and to the bottom end 15. The aperture 11 includes a first segment 52 extending along the first longitudinal axis 21 and a second segment 54 extending along the second longitudinal axis 27. Bend portion 23 is supported by the tip portion 17 to prevent flexure of the needle 9. Preferably, first portion 19 and second portion 25 form an acute angle of between twenty-five to forty-five degrees at bend portion 23.

As illustrated in FIG. 1, a topmost portion 29 of the tip 17 has a trapezoidal shaped vertical cross-section. A bottom most portion 31 is cylindrically shaped having a rectangular vertical cross-section. As shown in FIGS. 1 and 2, the tip 17 includes a flat top end 33 having a circular configuration through which the needle 9 extends. A horizontal cross-section 35 of the topmost portion 29 of the tip 17 would have an ovoidal shape.

As illustrated in FIG. 3, an angled syringe needle adapter 2 includes an externally threaded cylindrical hub 4 at the bottom end thereof. A solid upper portion 8 of the adapter 2 includes a flanged portion 10 extending out from middle of the adapter 2 above the solid lower hub 4 and below the solid upper portion 8 allowing a user to grip the adapter 2. The solid portion 8 includes a cylindrically shaped externally top threaded portion 12 for allowing an internally threaded hub H of an existing needle N to be attached thereto (see FIG. 4). An aperture 16 extending through the adapter 2 has a first portion 18 extending in a first linear direction 20 from a top opening 22 to a bend 24 located within said solid top portion 8 as illustrated in FIGS. 3 and 4. A second portion 26 of the aperature 16 located below the bend 24 extends in a second linear direction 28 from the bend 24 to a bottom opening 30 located on the bottom of the solid hub 4.

As the needle N is placed over the tip 14, a back end B of the needle N introduced through the top opening 22 travels within the first portion 18 of the aperture 16 in the first linear direction 20 until it reaches the bend 24. From the bend 24, the back end B of the needle N is diverted at an acute angle and moves in the second linear direction 28 towards the bottom opening 30.

It is to be understood that the present invention is not limited to the embodiments described above, but encompasses any and all embodiments within the scope of the following claims.

We claim:

1. An angled needle assembly for use with a dental syringe, said assembly comprising:

a needle having an aperture running therethrough, said needle further having a first portion, a second portion, and a bent portion, said bent portion joining said first portion to said second portion at an angle, said first portion terminating at a needle tip; and a rigid needle support body including,
 a threaded hub at a bottom end of said rigid needle support body through which said second portion of said needle passes, and
 a rigid tip portion at a top end of said rigid needle support body from which said first portion of said needle extends, said rigid tip portion including a channel firmly contacting said bent portion of said needle to prevent flexure of said needle.

2. The angled needle assembly according to claim 1, wherein said angle is between twenty-five and forty-five degrees.

3. The angled needle assembly according to claim 1, wherein said needle tip is bevelled.

4. The angled needle assembly according to claim 1, wherein said rigid needle support body is constructed of aluminum.

5. The angled needle assembly according to claim 1, wherein said needle support body is constructed of plastic.

6. The angled needle assembly according to claim 1, wherein said rigid tip portion has a bevelled top, said first portion of said needle extending from said bevelled top, and said rigid tip portion has a trapezoidal vertical cross-section.

7. The angled needle assembly according to claim 1, wherein said rigid tip portion includes a portion thereof having an ovoidal shaped horizontal cross-section.

\* \* \* \* \*